(12) United States Patent
Cho et al.

(10) Patent No.: US 7,013,708 B1
(45) Date of Patent: Mar. 21, 2006

(54) CARBON NANOTUBE SENSORS

(75) Inventors: Kyeongjae Cho, Palo Alto, CA (US); Shu Peng, Cupertino, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 657 days.

(21) Appl. No.: 10/194,916

(22) Filed: Jul. 11, 2002

(51) Int. Cl.
*G01N 7/00* (2006.01)
*D01F 9/12* (2006.01)

(52) U.S. Cl. .................. 73/31.05; 257/414; 423/447.2; 428/367

(58) Field of Classification Search ............... 73/31.05; 257/414; 423/447.1, 447.2, 447.3; 428/367
See application file for complete search history.

(56) References Cited

U.S. PATENT DOCUMENTS

| | | | |
|---|---|---|---|
| 4,495,793 A | 1/1985 | Hager | 73/23 |
| 5,436,167 A | 7/1995 | Robillard | 436/168 |
| 5,448,906 A | 9/1995 | Cheung | 73/31.06 |
| 5,626,650 A | 5/1997 | Rodriguez et al. | 95/116 |
| 5,653,951 A | 8/1997 | Rodriguez et al. | 423/439 |
| 5,866,434 A | 2/1999 | Massey et al. | 436/526 |
| 6,159,742 A | 12/2000 | Lieber et al. | 436/164 |
| 6,162,926 A | 12/2000 | Murphy et al. | 548/417 |
| 6,231,980 B1 * | 5/2001 | Cohen et al. | 428/402 |
| 6,528,020 B1 * | 3/2003 | Dai et al. | 422/98 |
| 6,894,359 B1 * | 5/2005 | Bradley et al. | 257/414 |
| 2003/0134433 A1 * | 7/2003 | Gabriel et al. | 436/518 |

FOREIGN PATENT DOCUMENTS

DE 10118200 A1 * 10/2002

OTHER PUBLICATIONS

Jul. 31, 2001, Robert J. Chen. Nathan R. Franklin. Jing Kong. Jien Cao. Thomas W. Tombler. Yuegang Zhang and Hongjie Dai. Molecular photodesorption from single-walled carbon nanotubes.

Jan. 22, 2001, Robert J. Chen, Yuegang Zhang, Dunwei Wang and Hongjie Dai. Noncovalent Sidewall Functionalization of Single-Walled Carbon Nanotubes for Protein Immobilization.

Jan. 28, 2000, Jing Kong, Nathan R. Franklin, Chongwu Zhou, Michael G. Chapline, Shu Peng. Kyeongjae Cho and Hongjie Dai, Nanotube Molecular Wires as Chemical Sensors.

Aug. 26, 2001, Hongjie Dai, A White Paper to Dr. David Patterson, MTO, DARPA, Integrated Nanotube-Electronic Noses and Bio-Chips (DNA-Chips & Protein Chips).

Nathan R. Franklin. Yiming Li, Robert J. Chen. Ali Javey and Hongjie Dai. Patterned Growth of Single-Walled Carbon Nanotubes on Full 4-inch Waters. Department of Chemistry, Stanford University, Stanford, CA 94305.

Jul. 21, 2000, Akira Koshio, Masayasu Inakuma, Zhong W. Wang. Toshiki Sugai and Hisanori Shinohara. In Situ Laser-Furnace TOF Mass Spectrometry of $C_{36}$ and the Large-Scale Production by Arc-Discharge J. Phys. Chem. B 2000. 104. 7908-7913.

* cited by examiner

*Primary Examiner*—Stanley S. Silverman
*Assistant Examiner*—Peter Lish
(74) *Attorney, Agent, or Firm*—Crawford Maunu PLLC; Robert J. Crawford (57) ABSTRACT

Nanotubes and nanotube-based devices are implemented in a variety of applications. According to an example embodiment of the present invention, a nanotube is doped with an impurity atom and used to detect the presence of a particular molecular species as a function of the particular molecular species bonding to the impurity atom. In one implementation, the doped nanotube responds electrically to the bonding of the particular molecular species to the impurity atom. With this approach, nanotubes such as single-walled carbon nanotubes can be doped to respond selectively to one or more types of molecular species.

33 Claims, 5 Drawing Sheets

FIG.1A

- = Boron
- = Carbon
- = Oxygen

FIG.1B

- = Boron
- = Carbon
- = Oxygen

FIG.2A

- = Carbon
- = Nitrogen
- = Oxygen

FIG.2B

- = Carbon
- = Nitrogen
- = Oxygen

FIG.3A

● = Boron
● = Carbon
◉ = Oxygen

FIG.3B

● = Boron
● = Carbon
◉ = Oxygen

FIG.4

◉ = Hydrogen
● = Boron
● = Carbon
◉ = Oxygen

FIG.5

◉ = Hydrogen
● = Carbon
◉ = Nitrogen
◉ = Oxygen

Plurality of Boron and Nitrogen

FIG. 11

Plurality of Boron and Nitrogen

FIG.12

CARBON NANOTUBE SENSORS

FIELD OF THE INVENTION

The present invention relates generally to carbon nanotube devices and more particularly to sensors employing carbon nanotubes.

BACKGROUND

Carbon nanotubes are unique carbon-based, molecular structures that exhibit interesting and useful electrical properties. Two general types of carbon nanotubes are referred to as multi-walled carbon nanotubes (MWNTs) and single-walled carbon nanotubes (SWNTs). SWNTs have a cylindrical sheet-like, one-atom-thick shell of hexagonally-arranged carbon atoms, and MWNTs are typically composed of multiple coaxial cylinders of ever-increasing diameter about a common axis. Thus, SWNTs can be considered to be the structure underlying MWNTs and also carbon nanotube ropes, which are uniquely-arranged arrays of SWNTs.

Carbon-based nanotubes are being studied for implementation in a variety of applications. These applications include, among others, chemical and bio-type sensing, field-emission sources, selective-molecule grabbing, nano-electronic devices, and a variety of composite materials with enhanced mechanical and electromechanical properties. More specifically, for example, in connection with chemical and biological detection, carbon nanotubes are being studied for applications including medical devices, environmental monitoring, medical/clinical diagnosis and biotechnology for gene mapping and drug discovery. For general information regarding carbon nanotubes, and for specific information regarding SWNTs and their applications, reference may be made generally to "Carbon Nanotubes: Synthesis, Structure, Properties and Applications," M. S. Dresselhaus, G. Dresselhaus and Ph. Avouris (Eds.), Springer-Verlag Berlin Heidelberg, New York, 2001; and "T. Single-shell Carbon Nanotubes of 1-nm Diameter," IIJIMA, S. & Ichihashi, Nature 363, 603–605 (1993).

Sensing molecular, chemical and biological species plays an important role in many industrial, agricultural, medical, and environmental processes. Detection of toxic gases, for example, provides a crucial measure of environmental pollution. In addition, detecting molecular concentrations can be useful in a variety of sensing and other applications. However, previously-available nanotubes have been difficult to manufacture and implement in a variety of such applications.

SUMMARY

The present invention is directed to overcoming the above-mentioned challenges and others related to carbon nanotube devices and their implementations. The present invention is exemplified in a number of implementations and applications, some of which are summarized below.

According to an example embodiment of the present invention, a nanotube device includes a carbon nanotube having at least one dopant therein, such as Boron or Nitrogen. The doped nanotube exhibits a detectable electrical response when introduced to a molecular species. In one implementation, the carbon nanotube is a single-walled carbon nanotube (SWNT), with the dopant being in the wall of the SWNT. With these approaches, the presence of the molecular species can readily detected by detecting the electrical response of the doped nanotube.

In another example embodiment of the present invention, a molecular sensor device includes one or more carbon nanotubes, each having opposite ends and being doped with an impurity atom. The one or more carbon nanotubes is adapted for coupling to a molecular species via the impurity atom (e.g., with the impurity atom bonding to an atom of the molecular species). Electrodes are coupled at each end of the one or more carbon nanotubes, and a detection circuit is coupled to the electrodes. The one or more carbon nanotubes are adapted for exhibiting an electrical response to the molecular species being coupled thereto, and the detection circuit is adapted for detecting the response. With this approach, the detected response can be used to identify the presence of the molecules.

In another example embodiment of the present invention, a nanotube sensor device is manufactured having a doped nanotube adapted for detecting the presence of a particular molecular species. The nanotube is doped with one or more impurity atoms, and a circuit is electrically coupled across the doped nanotube for detecting an electrical characteristic of the doped nanotube that is responsive to the impurity atom coupling to a molecular species. In one implementation, the nanotube is doped to a concentration that is selected to cause the nanotube to respond electrically to a particular molecular species (e.g., wherein different doping concentrations cause the nanotube to respond differently to different molecular species).

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for a variety of different types of devices, and the invention has been found to be particularly suited for carbon nanotube-based sensors and sensing applications, such as for sensing molecular, chemical and biological species. While the present invention is not necessarily limited to such applications, various aspects of the invention may be appreciated through a discussion of various examples using this context.

In connection with an example embodiment of the present invention, it has been discovered that carbon nanotubes having particular atoms doped thereto exhibit a detectable electrical response to selected molecules. Based on this discovery, carbon nanotubes can be used for the detection of diverse gas species, for example, with specific impurity atoms or complexes doped into the carbon nanotubes. The doping may be effected, for example, using substitutional, external and/or internal doping. In connection with this example embodiment, it has been discovered that such doped carbon nanotubes exhibit charge carrier characteristics that are a function of the dopants and that change when the doped nanotube is exposed to selected molecular species. The detectable electrical response can be monitored and used, for example, to detect the presence, location and/or concentration of the selected molecules.

In one implementation, a carbon-based nanotube, such as a SWNT, is doped with elements such as Boron or Nitrogen, thus forming nanotubes having structures such as BN, $BC_3$ and $B_xC_yN_z$. In another implementation, a composite $B_xC_yN_z$ nanotube has relative ratios of Boron, carbon and Nitrogen atoms (x:y:z) selected for one or more of a variety of implementations. In still another implementation, electrical coupling is made across the doped carbon nanotube with electrodes at opposite ends of the nanotube with electrical characteristics of the carbon nanotube being detected via the electrodes. With these approaches, doped carbon nanotubes can be used to detect the presence and/or other attributes of a variety of molecules.

In connection with another example embodiment of the present invention, it has been discovered that gas molecules can be detected using an intrinsic nanotube having Boron and/or Nitrogen atoms doped thereto. For instance, carbon monoxide (CO) can be detected as a change in conductance of a carbon nanotube doped with Boron, Nitrogen or a combination thereof. A variety of other gas molecules, such as aerosols, Nitrogen oxides, sulfur oxides and volatile organic compounds (VOC's) can similarly be detected using a doped nanotube. The detection of such gas molecules has typically been difficult using intrinsic carbon nanotubes. With this approach, gas detection in commercial, residential and other applications can be effected using a sensing device including a doped carbon nanotube.

In a more particular example embodiment of the present invention, the sensitivity of a carbon nanotube device to particular molecular species is set by doping the carbon nanotube to a particular concentration using one or more selected dopants. In connection with this example embodiment, it has been discovered that the selectivity of the doped carbon nanotube to specific molecules can be set by controlling the configuration and relative ratio of impurity atoms that reside on and/or in the doped nanotube. In one particular implementation, a carbon nanotube is doped to a specific concentration of Boron. In another particular implementation, a carbon nanotube is doped to a specific concentration of Nitrogen. In another particular implementation, a carbon nanotube is doped with both Boron and Nitrogen to respective selected concentrations. With each of these approaches, the particular concentrations can be readily determined for sensing a particular type of molecule with readily available experimentation techniques. Carbon nanotubes doped using this approach exhibit a particular electrical response when introduced to one or more selected molecules as a function of the dopant concentration and ratio; therefore, carbon nanotubes are selectively tuned to be responsive to particular molecules.

FIGS. 1A through 11 show carbon nanotubes having one or more molecules doped thereto and each adapted for sensing one or more molecular species, with an example of such a species shown for each. Beginning with FIGS. 1A and 1B, a carbon nanotube 105 includes a Boron atom 110 doped thereto, according to another example embodiment of the present invention. The Boron atom 110 may, for example, substitute for a carbon atom within the carbon nanotube 105, with the Boron atom entering a covalently-bonded in-plane lattice site of the nanotube. In the implementation shown in FIG. 1A, a CO molecule 120 introduced to the doped carbon nanotube 105 bonds to the Boron atom 110, with the carbon site of the CO molecule being closer to the Boron atom than the Oxygen site of the CO molecule is. In the implementation shown in FIG. 1B, a CO molecule 130 introduced to the doped carbon nanotube 105 bonds to the Boron atom 110, with the Oxygen site of the CO molecule being closer to the Boron atom than the carbon site of the CO molecule is. With either of these implementations, the bonding of the CO molecule to the carbon nanotube 105 causes a change in conductance of the nanotube, which is detected and used to detect the presence of the bonded CO molecule. In one implementation, such a Boron-doped nanotube 105 exhibits a binding energy of about 0.85 eV and an electron charge transfer of about 0.59 el/CO, which impart an electrical characteristic to the carbon nanotube that can be detected, for example, when a CO molecule is bonded to the Boron.

In the example embodiments discussed below in connection with FIGS. 2A–11, a change in conductance of the carbon nanotubes may be detected and used to detect the presence of bonded CO or other molecules in a manner similar to that discussed above; however, certain discussion thereof is omitted for brevity.

Figure 1A:
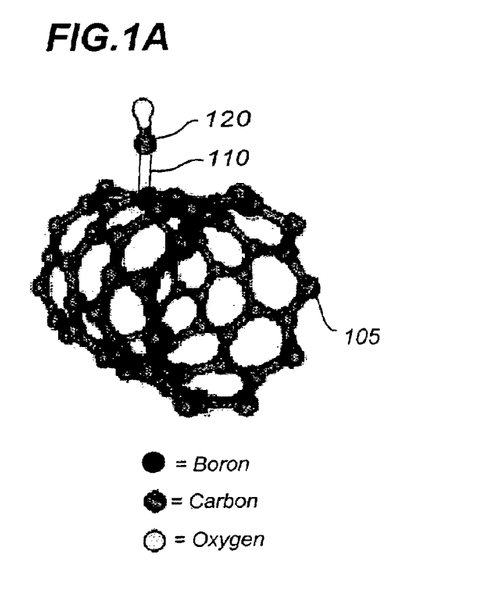
FIGS. 1A and 1B show a carbon nanotube having a Boron atom doped thereto and arranged for detecting one or more molecular species, according to an example embodiment of the present invention.
Figure 1B:
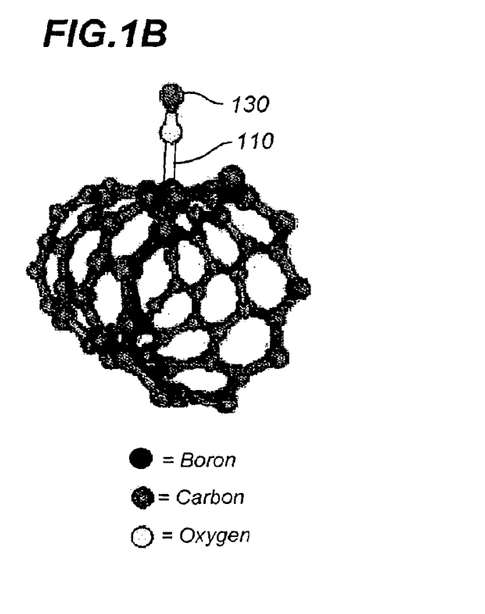
Figure 2A:
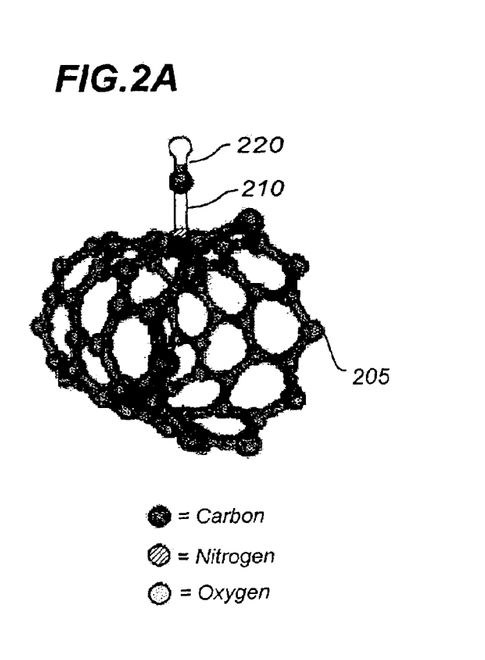
FIGS. 2A and 2B show a carbon nanotube having a Nitrogen atom doped thereto and arranged for detecting one or more molecular species, according to another example embodiment of the present invention.
Figure 2B:
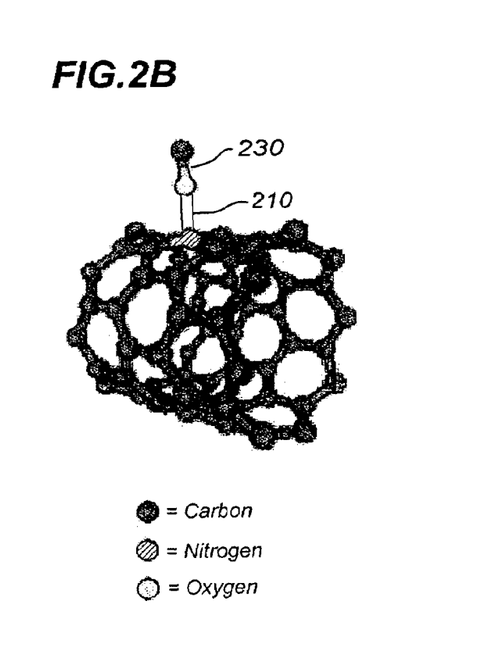

FIGS. 2A and 2B show another carbon nanotube 205 having a Nitrogen atom 210 doped thereto, according to another example embodiment of the present invention. The Nitrogen atom 210 may, for example, substitute for a carbon atom within the carbon nanotube 205 in a manner similar to that discussed above in connection with the Boron-atom substitution of FIGS. 1A–1B. In the implementation shown in FIG. 2A, a CO molecule 220 introduced to the doped carbon nanotube 205 bonds to the Nitrogen atom 210, with the carbon site of the CO molecule being closer to the Nitrogen atom than the Oxygen site of the CO molecule is. In the implementation shown in FIG. 2B, a CO molecule 230 introduced to the doped carbon nanotube 205 bonds to the Nitrogen atom 210, with the Oxygen site of the CO molecule being closer to the Nitrogen atom than the carbon site of the CO molecule is.

Figure 3A:
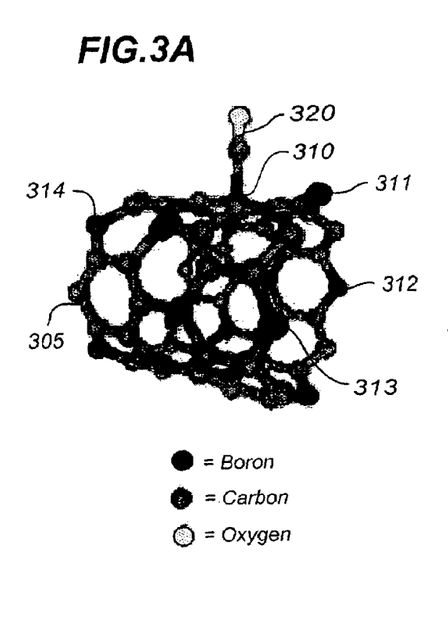
FIGS. 3A and 3B show a carbon nanotube having a plurality of Boron atoms doped thereto and arranged for detecting one or more molecular species, according to another example embodiment of the present invention.
Figure 3B:
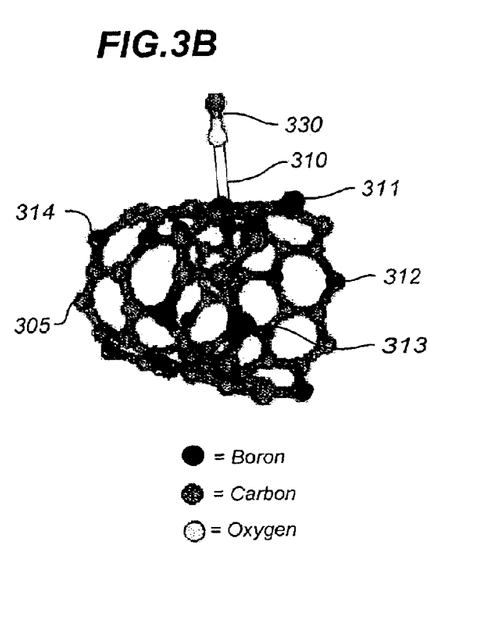

FIGS. 3A and 3B show a carbon nanotube 305 having a plurality of carbon atoms in the nanotube substituted with Boron atoms doped thereto (e.g., a $BC_3$ nanotube), according to another example embodiment of the present invention. Boron atoms 310–314 are labeled by way of example in each of the figures. Beginning with FIG. 3A, a CO molecule 320 introduced to the doped carbon nanotube 305 bonds to Boron atom 310, with the carbon site of the CO molecule being closer to the Boron atom than the Oxygen site of the CO molecule is. In FIG. 3B, a CO molecule 330 introduced to the doped carbon nanotube 305 bonds to the Boron atom 310, with the Oxygen site of the CO molecule being closer to the Nitrogen atom than the carbon site of the CO molecule is.

Figure 4:
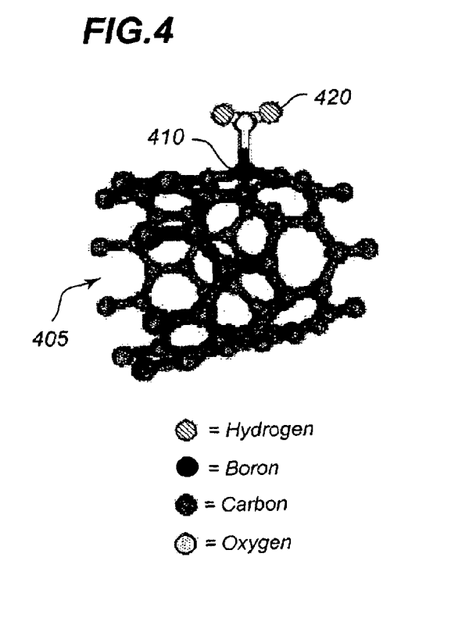
FIG. 4 shows a carbon nanotube having a Boron atom doped thereto and arranged for detecting one or more molecular species, according to another example embodiment of the present invention.

FIG. 4 shows a carbon nanotube 405 having a Boron atom 410 doped thereto, according to another example embodiment of the present invention. The Boron atom 410 may, for example, substitute for a carbon atom within the carbon nanotube 405 in a manner similar to that discussed above in connection with the Boron-atom substitution of FIGS. 1A–1B. An $H_2O$ molecule 420 introduced to the doped carbon nanotube 405 bonds to the Boron atom 410 at an Oxygen atom of the $H_2O$ molecule. In another implementation, the doped carbon nanotube 405 is adapted to bond to one or more other types of ionic molecules, in addition to $H_2O$.

Figure 5:
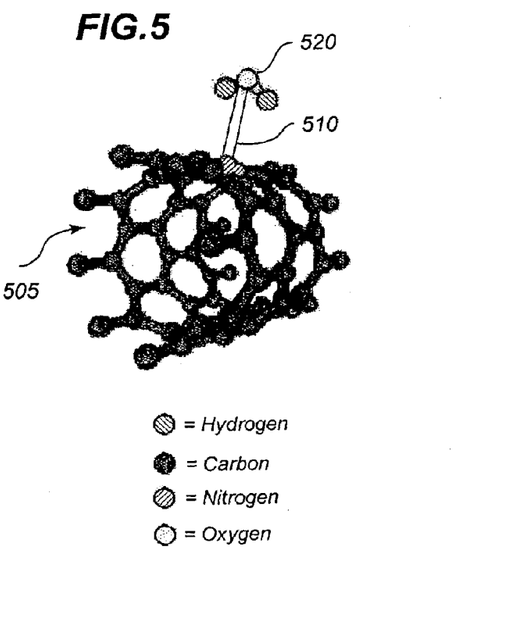
FIG. 5 shows a carbon nanotube having a Nitrogen atom doped thereto and arranged for detecting one or more molecular species, according to another example embodiment of the present invention.

FIG. 5 shows a carbon nanotube 505 having a Nitrogen atom 510 doped thereto, according to another example embodiment of the present invention. The Nitrogen atom 510 may, for example, substitute for a carbon atom within the carbon nanotube 505 in a manner similar to that discussed above in connection with the Boron-atom substitution of FIGS. 1A–1B. An $H_2O$ molecule 520 introduced to the doped carbon nanotube 505 bonds to the Nitrogen atom 510 at an Oxygen atom of the $H_2O$ molecule.

Figure 6:
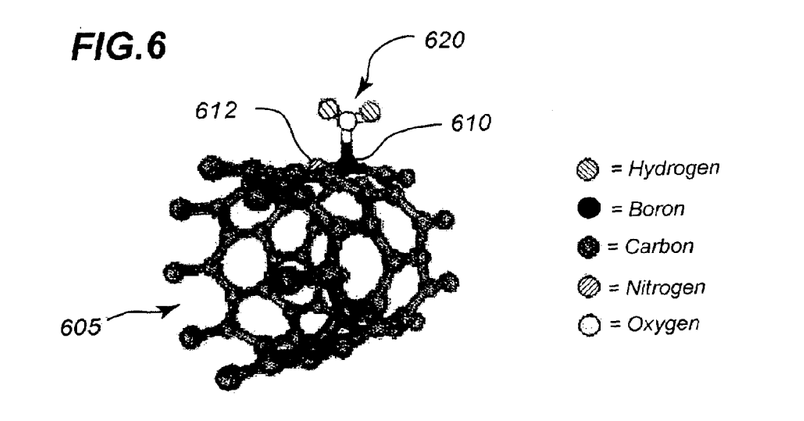
FIG. 6 shows a carbon nanotube having Boron and Nitrogen atoms doped thereto and arranged for detecting one or more molecular species coupled via a Boron atom, according to another example embodiment of the present invention.

FIG. 6 shows a carbon nanotube 605 having a Boron atom 610 and a Nitrogen atom 612 doped thereto, according to another example embodiment of the present invention. The Boron and Nitrogen atoms 610 and 612 may, for example, each substitute for a carbon atom within the carbon nanotube 605 in a manner similar to that discussed above in connection with the Boron-atom substitution of FIGS. 1A–1B. An $H_2O$ molecule 620 introduced to the doped carbon nanotube 605 bonds to the Boron atom 610 at an Oxygen atom of the $H_2O$ molecule.

Figure 7:
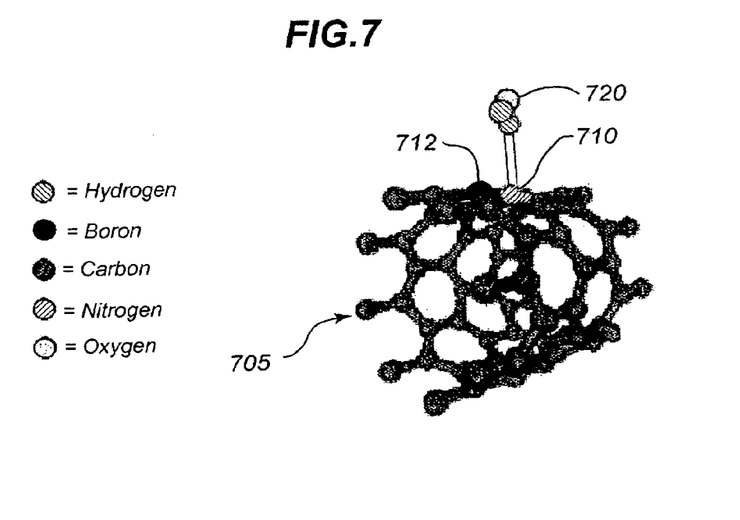
FIG. 7 shows a carbon nanotube having Boron and Nitrogen atoms doped thereto and arranged for detecting one or more molecular species coupled via a Nitrogen atom, according to another example embodiment of the present invention.

FIG. 7 shows a carbon nanotube 705 having a Nitrogen atom 710 and a Boron atom 712 doped thereto, according to another example embodiment of the present invention. The Nitrogen and Boron atoms 710 and 712 may, for example, each substitute for a carbon atom within the carbon nanotube 705 in a manner similar to that discussed above in connection with the Boron-atom substitution of FIGS. 1A–1B. An $H_2O$ molecule 720 introduced to the doped carbon nanotube 705 bonds to the Nitrogen atom 710 at an Oxygen atom of the $H_2O$ molecule.

Figure 8:
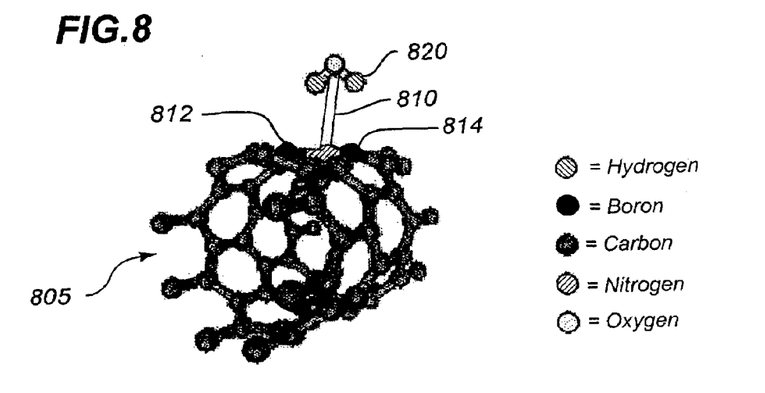
FIG. 8 shows a carbon nanotube having Boron and Nitrogen atoms doped thereto and arranged for detecting one or more molecular species coupled via a Nitrogen atom, according to another example embodiment of the present invention.

FIG. 8 shows a carbon nanotube 805 having a Nitrogen atom 810 and two Boron atoms 812 and 814 doped thereto, according to another example embodiment of the present invention. The Nitrogen and Boron atoms 810, 812 and 814 may, for example, each substitute for a carbon atom within the carbon nanotube 805 in a manner similar to that discussed above in connection with the Boron-atom substitution of FIGS. 1A–1B. An $H_2O$ molecule 820 introduced to the doped carbon nanotube 805 bonds to the Nitrogen atom 810 at an Oxygen atom of the $H_2O$ molecule.

Figure 9:
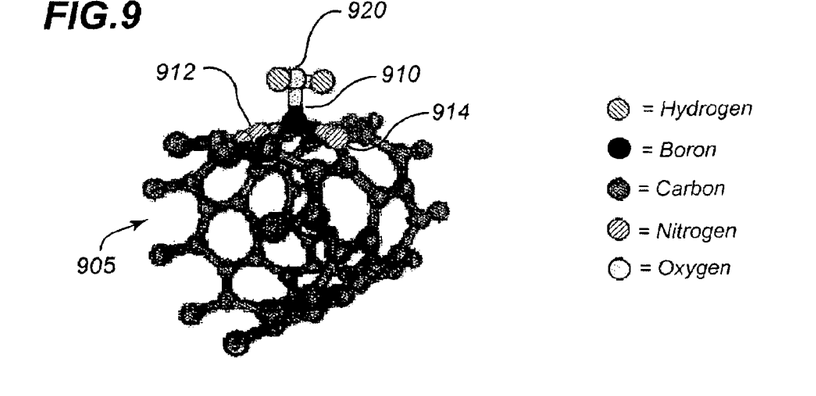
FIG. 9 shows a carbon nanotube having Boron and Nitrogen atoms doped thereto and arranged for detecting one or more molecular species coupled via a Boron atom, according to another example embodiment of the present invention.

FIG. 9 shows a carbon nanotube 905 having a Boron atom 910 and two Nitrogen atoms 912 and 914 doped thereto, according to another example embodiment of the present invention. The Boron and Nitrogen atoms 910, 912 and 914 may, for example, each substitute for a carbon atom within the carbon nanotube 905 in a manner similar to that discussed above in connection with the Boron-atom substitution of FIGS. 1A–1B. An $H_2O$ molecule 920 introduced to the doped carbon nanotube 905 bonds to the Boron atom 910 at an Oxygen atom of the $H_2O$ molecule.

Figure 10:
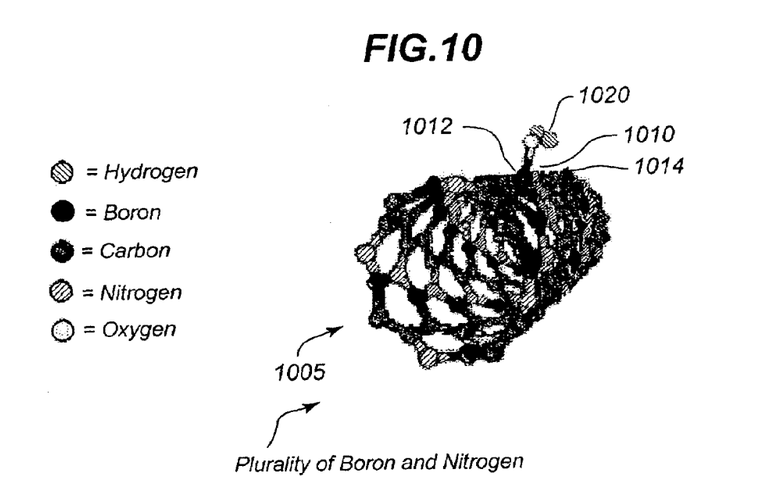
FIG. 10 shows a carbon nanotube having Boron and Nitrogen atoms doped thereto and arranged for detecting one or more molecular species coupled via a Boron atom, according to another example embodiment of the present invention.

FIG. 10 shows a carbon nanotube 1005 having a plurality of Boron and Nitrogen atoms doped thereto, including Boron atom 1010 that forms part of a $BN_2$ group with Nitrogen atoms 1012 and 1014, according to another example embodiment of the present invention. The Boron and Nitrogen atoms 1010, 1012 and 1014 may, for example, substitute for a carbon atom within the carbon nanotube 1005 in a manner similar to that discussed above in connection with the Boron-atom substitution of FIGS. 1A–1B. An $H_2O$ molecule 1020 introduced to the doped carbon nanotube 1005 bonds to the Boron atom 1010 at an Oxygen atom of the $H_2O$ molecule.

Figure 11:
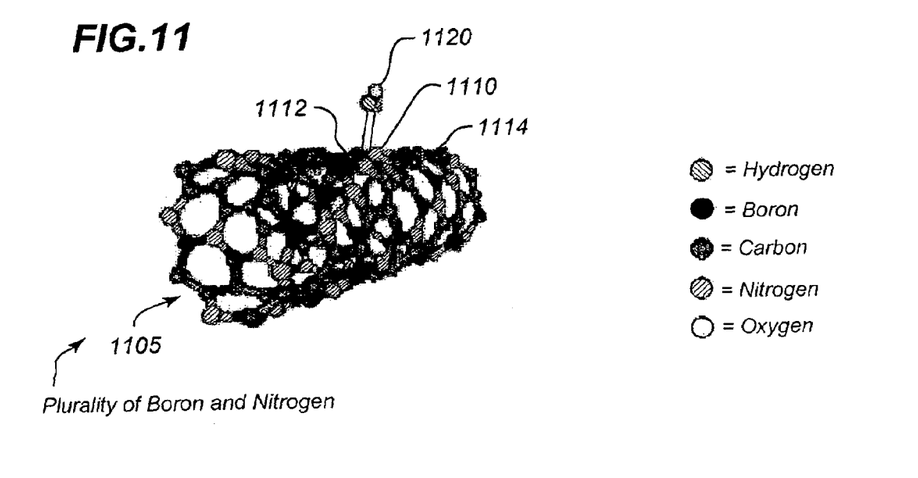
FIG. 11 shows a carbon nanotube having Boron and Nitrogen atoms doped thereto and arranged for detecting one or more molecular species coupled via a Nitrogen atom, according to another example embodiment of the present invention.

FIG. 11 shows a carbon nanotube 1105 having a plurality of Nitrogen and Boron atoms doped thereto, including Nitrogen atom 1110 that forms part of a $B_2N$ group with Boron atoms 1112 and 1114, according to another example embodiment of the present invention. The Nitrogen atom 1110 may, for example, substitute for a carbon atom within the carbon nanotube 1105 in a manner similar to that discussed above in connection with the Boron-atom substitution of FIGS. 1A–1B. An $H_2O$ molecule 1120 introduced to the doped carbon nanotube 1105 bonds to the Boron atom 1010 at an Oxygen atom of the $H_2O$ molecule.

In another example embodiment of the present invention, a composite carbon nanotube device having both Boron and Nitrogen doped thereto (e.g., in a $B_xC_yN_z$ arrangement) functions as a bifunctional sensor for sensing toxic gas and humidity. The bifunctional sensor uses one or more of a variety of doped nanotube arrangements, depending upon the intended sensing application. In one instance, a single carbon nanotube is doped with one or more dopant types such that the doped carbon nanotube bonds to both toxic gas molecules and to water molecules. In this regard, one or more of the arrangements discussed in connection with FIGS. 1A–3B can be used for bonding to and detecting the presents of CO. Similarly, one or more of the arrangements discussed in connection with FIGS. 4–11 can be used for bonding to and detecting the presence of $H_2O$. By using a combination of dopant arrangements doped to a single nanotube, a multitude of molecules can be detected. In one implementation, a detectable electrical characteristic of a doped nanotube being in a first range is an indication of a CO molecule bonding to a dopant therein, and the detectable electrical characteristic being in a second range is an indication of a $H_2O$ molecule bonding to a dopant therein. In a more particular implementation, a detectable electrical characteristic of the doped nanotube being in a third range is an indication of both CO molecules and $H_2O$ molecules bonded to the carbon nanotube.

In another bifunctional sensor implementation, a single dopant type is doped to a carbon nanotube that is arranged to bond to both CO and $H_2O$ via the single dopant type. For instance, a Boron-doped nanotube (e.g., nanotube 105 in FIGS. 1A and 1B and/or nanotube 405 in FIG. 4) can be used to bond to both CO and $H_2O$, with one or more Boron atoms substituting for carbon atoms on the nanotube. The doped nanotube exhibits a detectable electrical response that is distinguishable between responses corresponding to bonds made to CO, $H_2O$ and/or to both CO and $H_2O$. A detectable electrical characteristic of the doped carbon nanotube device is monitored and used to detect the presence of one or both of CO and $H_2O$.

Figure 12:
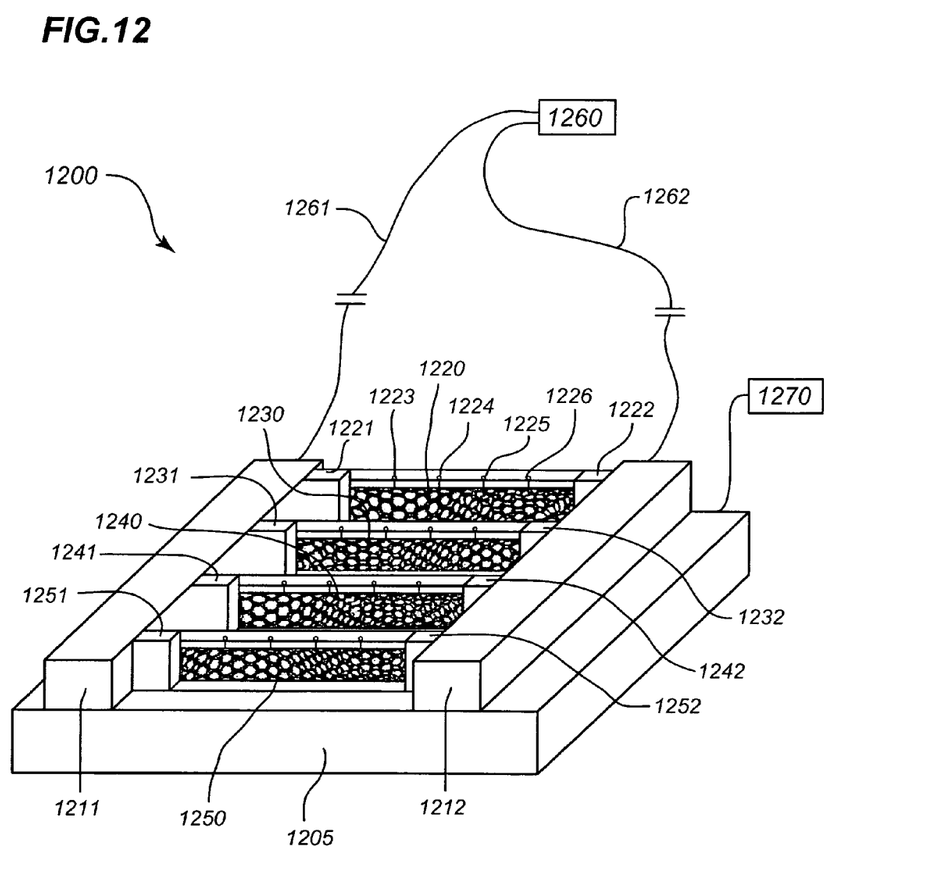
FIG. 12 shows a sensor having a plurality of carbon nanotubes having one or more dopants, according to another example embodiment of the present invention.

FIG. 12 shows a bifunctional sensor 1200 having an array of diversely functionalized nanotubes that is configured and arranged to detect different kinds of chemical species, such as carbon monoxide and water, according to another example embodiment of the present invention. Each nanotube shown in the sensor 1200 may, for example, be arranged consistently with one of the nanotubes described in connection with one or more of the example embodiments discussed herein, including those discussed in connection with the figures above. The bifunctional sensor 1200 includes a plurality of nanotubes, with nanotubes 1220, 1230, 1240 and 1250 being shown formed over a substrate 1205, such as silicon or quartz. Each of the nanotubes 1220, 1230, 1240 and 1250 has electrodes 1221 and 1222; 1231 and 1232; 1241 and 1242; and 1251 and 1252, respectively, at opposite ends thereof. The electrodes are coupled to interconnects 1211 and 1212, which are in turn electrically coupled to a detection arrangement 1260 via couplers 1261 and 1262. The detection arrangement 1260 may, for example, include circuitry for detecting the conductance across the nanotubes. Using nanotube 1220 as an example, molecules 1223, 1224, 1225 and 1226 are shown bonded thereto, such as via bonds made to Boron or Nitrogen-type dopants on the nanotube 1220.

In a more particular implementation, the nanotubes of the bifunctional sensor 1200 are doped at selected locations such that the detection of the presence of a particular molecule can be used to detect the location of the particular molecule. For example, referring to nanotube 1220 as an example, dopants are doped to the nanotube 1220 at locations immediately adjacent to the molecules 1223, 1224, 1225 and 1226. Such location-specific doping may be achieved, for example, using a high-resolution instrument such as a focused ion beam to selectively deposit a catalytic nanoparticle on selected locations of the nanotube, with subsequent introduction (e.g., growth) of a dopant to the nanotube. A change in an electrical characteristic of the nanotube is then used to detect the presence of the molecules being at one or more of the locations. In a more particular implementation, at least two of the nanotubes 1220, 1230, 1240 and 1250 are doped differently, such that each responds differently to bonding to molecules. By detecting an electrical change corresponding to one of the doped nanotubes bonding to a molecule, the location of the bonded molecule can be identified as being adjacent to the nanotube exhibiting the response.

The carbon nanotube devices used in connection with the example embodiments and implementations thereof and discussed herein, such as the device 1200 shown in FIG. 12, can be implemented in a variety of applications. For example, CO detection for households, confined spaces, automobile emissions and power plant emissions can be effected using one or more of the doped carbon nanotube devices discussed herein. Similarly, $H_2O$ detection for humidity sensors and exhaust gas analyzers can also be effected using one or more of the doped carbon nanotube devices discussed herein.

In another example embodiment of the present invention, different impurity atoms are doped at different locations on a nanotube to form one or more p-n junctions along the nanotube. The doping may, for example, be effected simultaneously. In connection with this example embodiment, it has been discovered that such a p-n junction exhibits a nonlinear sensor response characteristic, which is useful for monitoring a change in the response characteristic. With this approach, the sensitivity and selectivity of a doped nanotube to a particular molecular species are such that a response of the nanotube to the species is readily detectable.

In still another example embodiment of the present invention, a nanotube sensor device is adapted for applying an electric pulse to a doped carbon nanotube for identifying the presence of chemical species. For instance, by applying a voltage pulse of a particular magnitude and shape to the doped carbon nanotube, the sensitivity of the doped carbon nanotube to particular molecular species can be tuned. Referring to FIG. 12, the pulse may, for example, by applied using a voltage supply 1270, optionally coupled to a portion of the device 1200 (e.g., to a conductor, or gate, in a portion of substrate below the carbon nanotubes). For more information regarding the use of such voltage pulses and corresponding output response of a doped carbon nanotube for detecting molecular species, reference may be made to FIG. 4 in Appendix B, discussed below.

Experimental Data

In connection with one or more of the example embodiments of the present invention and implementations thereof, the following experimental data shows additional applications to which one or more example embodiments of the present invention are directed. The detection capacity of example doped carbon nanotube devices to the presence of carbon monoxide or water molecules is compared to that of similar devices using intrinsic carbon nanotubes in Tables 1 and 2, attached hereto as Appendix A and fully incorporated herein by reference.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include modifying the nanotubes for sensing one or more particular molecular species, altering the circuit arrangements, using Boron-based nanotubes instead of carbon-based nanotubes, interchanging nanotube films and single nanotubes, and where appropriate, using SWNTs as building blocks for more complex devices. Moreover, in addition to the sensing agents described in the example embodiments and implementations above, other materials can be applied to the nanotubes and nanotube devices for tailoring their application. In addition, for general information regarding carbon nanotubes, and for specific information regarding implementations to which various example embodiments of the present invention may be directed, reference may be made to the attached Appendix B, which is fully incorporated herein by reference. Such modifications and changes do not depart from the true spirit and scope of the present invention, which is set forth in the following claims.

Sensing molecular, chemical and biological species plays an important role in many industrial, agricultural, medical, and environmental processes. Detection of toxic gases, for example, provides a crucial measure of environmental pollution. In addition, detecting molecular concentrations can be useful in a variety of sensing and other applications. However, previously-available nanotubes have been difficult to manufacture and implement in a variety of such applications, and in particular have been difficult to implement for the detection of different types of molecular species.

SUMMARY

The present invention is directed to overcoming the above-mentioned challenges and others related to carbon nanotube devices and their implementations. The present invention is exemplified in a number of implementations and applications, some of which are summarized below.

According to an example embodiment of the present invention, a nanotube device includes a carbon nanotube having at least one dopant therein, such as Boron or Nitrogen. The doped nanotube exhibits a detectable electrical response when introduced to a molecular species. In one implementation, the carbon nanotube is a single-walled carbon nanotube (SWNT), with the dopant being in the wall of the SWNT. With these approaches, the presence of the molecular species can readily be detected by detecting the electrical response of the doped nanotube.

In another example embodiment of the present invention, a molecular sensor device includes one or more carbon nanotubes, each having opposite ends and being doped with an impurity atom. The one or more carbon nanotubes is adapted for coupling to a molecular species via the impurity atom (e.g., with the impurity atom bonding to an atom of the molecular species). Electrodes are coupled at each end of the one or more carbon nanotubes, and a detection circuit is coupled to the electrodes. The one or more carbon nanotubes are adapted for exhibiting an electrical response to the molecular species being coupled thereto, and the detection circuit is adapted for detecting the response. With this approach, the detected response can be used to identify the presence of the molecules.

DETAILED DESCRIPTION

The present invention is believed to be useful for a variety of different types of devices, and the invention has been found to be particularly suited for carbon nanotube-based sensors and sensing applications, such as for sensing molecular, chemical and biological species. While the present invention is not necessarily limited to such applications, various aspects of the invention may be appreciated through a discussion of various examples using this context.

In connection with an example embodiment of the present invention, it has been discovered that carbon nanotubes having particular atoms doped thereto exhibit a detectable electrical response to selected molecules. Based on this discovery, carbon nanotubes can be used for the detection of diverse gas species, for example, with specific impurity atoms or complexes doped into the carbon nanotubes. The doping may be effected, for example, using substitutional doping (e.g., impurity species in a lattice site of the carbon nanotube), external doping (e.g., impurity species adsorbed on an outer surface of the carbon nanotube) and/or internal doping (e.g., impurity species adsorbed on an inner surface of the carbon nanotube). In connection with this example embodiment, it has been discovered that such doped carbon nanotubes exhibit charge carrier characteristics that are a function of the dopants and that change when the doped nanotube is exposed to selected molecular species. The detectable electrical response can be monitored and used, for example, to detect the presence, location and/or concentration of the selected molecules.

In one implementation, a carbon-based nanotube, such as a SWNT, is doped with elements such as Boron or Nitrogen, thus forming nanotubes having structures such as BN, $BC_3$ and $B_xC_yN_z$. In another implementation, a composite $B_xC_yN_z$ nanotube has relative ratios of Boron, carbon and Nitrogen atoms (x:y:z) selected for one or more of a variety of implementations. In still another implementation, electrical coupling is made across the doped carbon nanotube with electrodes at opposite ends of the nanotube with electrical characteristics of the carbon nanotube being detected via the electrodes. With these approaches, doped carbon nanotubes can be used to detect the presence and/or other attributes of a variety of molecules.

In another implementation, a carbon-based nanotube is doped with a plurality of atoms adapted to couple to a molecular species. When a gas having a relatively high concentration of the molecular species is introduced to the doped carbon nanotube, a relatively large number of the molecules couple to the doped atoms, causing a relatively large change in electrical response. When a gas having a relatively low concentration of the molecular species is introduced to the doped carbon nanotube, a relatively smaller number of the molecules couple to the doped atoms, causing a relatively smaller change in electrical response. In this regard, the concentration of molecular species in a particular gas being introduced to the doped carbon nanotube can be detected.

In connection with another example embodiment of the present invention, it has been discovered that gas molecules can be detected using an intrinsic nanotube (e.g., pure carbon) having Boron and/or Nitrogen atoms doped thereto. For instance, carbon monoxide (CO) can be detected as a change in conductance of a carbon nanotube doped with Boron, Nitrogen or a combination thereof. A variety of other gas molecules, such as aerosols and volatile organic compounds (VOC's) can similarly be detected using a doped nanotube. The detection of some of these types of gas molecules has typically been difficult using intrinsic carbon nanotubes. With this approach, gas detection in commercial, residential and other applications can be effected using a sensing device including a doped carbon nanotube.

In a more particular example embodiment of the present invention, the sensitivity of a carbon nanotube device to particular molecular species is set by doping the carbon nanotube to a particular concentration using one or more selected dopants. In connection with this example embodiment, it has been discovered that the selectivity of the doped carbon nanotube to specific molecules can be set by controlling the configuration and relative ratio of impurity atoms that reside on and/or in the doped nanotube. In one particular implementation, a carbon nanotube is doped to a specific concentration of Boron. In another particular implementation, a carbon nanotube is doped to a specific concentration of Nitrogen. In another particular implementation, a carbon nanotube is doped with both Boron and Nitrogen to respective selected concentrations. With each of these approaches, the particular concentrations can be readily determined for sensing a particular type of molecule with readily available experimentation techniques. Carbon nanotubes doped using this approach exhibit a particular electrical response when introduced to one or more selected molecules as a function of the dopant concentration and ratio; therefore, carbon nanotubes are selectively tuned to be responsive to particular molecules.

FIGS. 1A through 11 show carbon nanotubes having one or more molecules doped thereto and each adapted for sensing one or more molecular species, with an example of such a species shown for each. Beginning with FIGS. 1A and 1B, a carbon nanotube 105 includes a Boron atom 110 doped thereto, according to another example embodiment of the present invention. The Boron atom 110 may, for example, substitute for a carbon atom within the carbon nanotube 105, with the Boron atom entering a covalently-bonded in-plane lattice site of the nanotube. In the implementation shown in

What is claimed is:

1. A nanotube device comprising at least one doped carbon nanotube being configured and arranged to exhibit a detectable electrical response when introduced to a molecular species, the carbon nanotube being doped with a dopant selected from the group of Boron and Nitrogen, and being doped to a dopant concentration to effect a particular electrical response when the carbon nanotube is introduced to a selected molecular species.

2. The nanotube device of claim 1, wherein the carbon nanotube is doped to a dopant concentration such that the doped carbon nanotube responds electrically to CO.

3. The nanotube device of claim 2, wherein the carbon nanotube is doped to a dopant concentration such that the doped carbon nanotube responds electrically to $H_2O$.

4. The nanotube device of claim 1, wherein the carbon nanotube is doped to a dopant concentration such that the doped carbon nanotube responds electrically to $H_2O$.

5. The nanotube device of claim 1, further comprising an array of carbon nanotubes, each carbon nanotube being doped with an impurity atom and being configured and arranged to exhibit a detectable electrical response when introduced to a molecular species.

6. The nanotube device of claim 1, wherein the carbon nanotube is doped with at least two dopant types.

7. The nanotube device of claim 6, wherein the carbon nanotube is doped with Boron and Nitrogen.

8. The nanotube device of claim 1, wherein the carbon nanotube is doped with Boron atoms.

9. The nanotube device of claim 1, wherein the carbon nanotube is doped with Nitrogen atoms.

10. The nanotube device of claim 1, wherein the carbon nanotube is doped with a Boron-Nitrogen atom pair.

11. The nanotube device of claim 1, wherein the carbon nanotube is doped with a Boron-Nitrogen-Boron atom complex.

12. The nanotube device of claim 1, wherein the carbon nanotube is doped with a Nitrogen-Boron-Nitrogen complex.

13. The nanotube device of claim 1, wherein the carbon nanotube is doped with Boron and wherein a Boron atom of the doped carbon nanotube is configured and arranged to bond to an $H_2O$ molecule via the oxygen atom of the $H_2O$ molecule.

14. The nanotube device of claim 1, wherein the carbon nanotube is doped with Nitrogen and wherein a Nitrogen atom of the doped carbon nanotube is configured and arranged to bond to an $H_2O$ molecule via the oxygen atom of the $H_2O$ molecule.

15. The nanotube device of claim 1, wherein a dopant atom of the doped carbon nanotube is configured and arranged to bond to a CO molecule via the carbon atom of the CO molecule.

16. The nanotube device of claim 1, wherein a dopant atom of the doped carbon nanotube is configured and arranged to bond to a CO molecule via the oxygen atom of the CO molecule.

17. The nanotube device of claim 1, wherein the carbon nanotube is a single-walled carbon nanotube.

18. The nanotube device of claim 17, wherein the dopant is disposed in the wall of the carbon nanotube.

19. The nanotube device of claim 17, wherein the dopant is bonded to a carbon molecule in the wall of the carbon nanotube and extends outward from the wall.

20. The nanotube device of claim 1, wherein the nanotube is doped with dopants that form a p-n junction on the nanotube, the p-n junction having nonlinear sensor characteristics and being configured and arranged to electrically respond upon exposure to selected molecules.

21. The nanotube device of claim 1, wherein the doped carbon nanotube is configured and arranged to electrically respond to an ionic compound.

22. The nanotube device of claim 1, wherein the carbon nanotube is doped by replacing a carbon atom in the crystalline structure of the nanotube.

23. The nanotube device of claim 1, further comprising a detection circuit adapted for detecting the detectable electrical response of the carbon nanotube.

24. The nanotube device of claim 1, wherein the doped carbon nanotube is substitutionally doped.

25. The nanotube device of claim 1, wherein the doped carbon nanotube is externally doped.

26. The nanotube device of claim 1, wherein the doped carbon nanotube is internally doped.

27. A molecular sensor comprising:
at least one carbon nanotube having opposite ends and being configured and arranged to exhibit a detectable electrical response when introduced to a molecular species, the at least one carbon nanotube being doped with a dopant selected from the group of Boron and Nitrogen, and being doped to a dopant concentration to effect a particular electrical response when the carbon nanotube is introduced to a selected molecular species;
electrodes coupled to each end of the at least one carbon nanotube; and
a detection circuit coupled to the electrodes and configured and arranged to detect the electrical response of the at least one carbon nanotube to the molecular species.

28. The molecular sensor of claim 27, wherein the detection circuit is configured and arranged to detect a change in the detected electrical characteristic, the change in the detected electrical characteristic being responsive to molecules introduced to the carbon nanotube.

29. The molecular sensor of claim 28, wherein the detection circuit is configured and arranged to detect the concentration of the molecules introduced to the carbon nanotube as a function of the detected electrical characteristic.

30. The molecular sensor of claim 28, wherein the detection circuit is configured and arranged to detect the composition of the molecules introduced to the carbon nanotube as a function of the detected electrical characteristic.

31. The nanotube device of claim 27, wherein the carbon nanotube is doped with dopant atoms at different locations on the carbon nanotube and wherein the detection circuit is configured and arranged to detect an electrical response of the nanotube to a molecule bonding to one of the dopant atoms and to detect the physical location of the molecule bonding to one of the dopant atoms as a function of the electrical response.

32. The nanotube device of claim 27, further comprising a voltage application circuit adapted for applying a voltage pulse to the carbon nanotube for identifying a molecular species.

33. The nanotube device of claim 32, wherein the voltage application circuit is adapted for altering an electrical characteristic of the carbon nanotube such that an electrical response of the carbon nanotube to a particular molecular species can be detected by the detection circuit.

* * * * *

UNITED STATES PATENT AND TRADEMARK OFFICE
CERTIFICATE OF CORRECTION

PATENT NO.       : 7,013,708 B1
APPLICATION NO.  : 10/194916
DATED            : March 21, 2006
INVENTOR(S)      : Cho et al.

It is certified that error appears in the above-identified patent and that said Letters Patent is hereby corrected as shown below:

Col. 1, lines 48 and 49: "such applications." should read --such applications, and in particular have been difficult to implement for the detection of different types of molecular species.--.

Col. 3, lines 53-54: "using substitutional," should read --using substitutional doping (*e.g.*, impurity species in a lattice site of the carbon nanotube), external doping (*e.g.*, impurity species adsorbed on an outer surface of the carbon nanotube) and/or internal doping (*e.g.*, impurity species adsorbed on an inner surface of the carbon nanotube).--

Col. 4, insert between lines 7-8: --In another implementation, a carbon-based nanotube is doped with a plurality of atoms adapted to couple to a molecular species. When a gas having a relatively high concentration of the molecular species is introduced to the doped carbon nanotube, a relatively large number of the molecules couple to the doped atoms, causing a relatively large change in electrical response. When a gas having a relatively low concentration of the molecular species is introduced to the doped carbon nanotube, a relatively smaller number of the molecules couple to the doped atoms, causing a relatively smaller change in electrical response. In this regard, the concentration of molecular species in a particular gas being introduced to the doped carbon nanotube can be detected.--

Col. 4, line 17: "The detection of such" should read --The detection of some of these types of--.

Col. 9, lines 27-67: delete.

Col. 10, lines 1-67: delete.

Col. 11, lines 1-29: delete.

Col. 13, line 11, Claim 31: "The nanotube device" should read --The molecular sensor--.

Col. 14, line 4, Claim 32: "The nanotube device" should read --The molecular sensor--.

UNITED STATES PATENT AND TRADEMARK OFFICE
CERTIFICATE OF CORRECTION

PATENT NO. : 7,013,708 B1
APPLICATION NO. : 10/194916
DATED : March 21, 2006
INVENTOR(S) : Cho et al.

It is certified that error appears in the above-identified patent and that said Letters Patent is hereby corrected as shown below:

Col. 14, line 8, Claim 33: "The nanotube device" should read --The molecular sensor--.

Signed and Sealed this

Tenth Day of April, 2007

JON W. DUDAS
*Director of the United States Patent and Trademark Office*